(12) United States Patent
Acevedo et al.

(10) Patent No.: US 7,232,891 B2
(45) Date of Patent: *Jun. 19, 2007

(54) ANTI-HUMAN LUTEINIZING HORMONE-RELATED ANTIBODIES AND USES THEREOF

(75) Inventors: Hernan Acevedo, Pittsburgh, PA (US); Alexander Krichevsky, New York, NY (US)

(73) Assignees: The Trustees of Columbia University in the city of New York, New York, NY (US); Allegheny-Singer Research Institute, Pittsburgh, PA (US)

( * ) Notice: Subject to any disclaimer, the term of this patent is extended or adjusted under 35 U.S.C. 154(b) by 687 days.

This patent is subject to a terminal disclaimer.

(21) Appl. No.: 10/164,914

(22) Filed: Jun. 6, 2002

(65) Prior Publication Data

US 2003/0092082 A1    May 15, 2003

Related U.S. Application Data

(63) Continuation of application No. 08/478,431, filed on Jun. 7, 1995, now Pat. No. 6,403,326, which is a continuation of application No. 08/062,925, filed on May 13, 1993, now abandoned.

(51) Int. Cl.
 *C07K 16/00* (2006.01)
(52) U.S. Cl. .............................. 530/388.1; 530/388.24; 530/388.15; 436/536; 436/548
(58) Field of Classification Search ............... 435/7.23, 435/7.9, 64, 70.21, 240.27; 436/536, 548; 530/388.1, 388.24, 388.15
See application file for complete search history.

(56) References Cited

U.S. PATENT DOCUMENTS

| 4,460,561 A | 7/1984 | Goldenberg ................ 424/1.1 |
| 4,510,244 A | 4/1985 | Parks ....................... 435/172.2 |
| 6,403,326 B1* | 6/2002 | Acevedo et al. .......... 435/7.23 |

OTHER PUBLICATIONS

Szende et al (PNAS USA. 1991, 88:4153-4156).*
Xiang et al (Clin. Expl. Metastasis. 1987, 5:35-42).*
Tsujisaki et al. Clin. Exp. Immunol. 1991. 85:3-8.*
Wright et al. Cancer. 1990. 66:1242-1252.*
Keydar et al. PNAS USA. 1989. 86:1362-1366.*
Parratto and Kimura. J Cellular Biochemistry. 1988. 36:311-322.*
Cordon-Caro et al. Cancer Research. 1991. 51:6372-6380.*
Lin et al. Journal of Occupational Medicine. 1990. 32:910-916.*
Brown. Cancer Research. 1983, 43:2113-2120.*
Leslie et al. Am J Clin Pathol. 1990, 94:8-13.*
Alonso-Whipple C., Couet M.L., Doss R., Koziarz J., Ogunro E.A. and Crowley W.D. Jr. (1988) Epitope mapping of human luteinizing hormone using monoclonal antibodies, Endocrinology 123:1854-1860 (Exhibit 3).

Berger P., Panmoung W., Khaschab D., Mayrigger B., Wick G. (1988) Antigenic features of human follicle stimulating hormone delineated by monoclonal antibodies and construction of an immunoradiometric assay. Endocrinology 123:2351-2359 (Exhibit 4).
Cole L.A., J.H. Nam, Chambersm J.T. and Schwartz P.E. (1990) Urinary gonadotopin fragment, a new tumor marker. II. Differentiating a benign from a malignant pelvic mass. Gynecol. Oncol. 36:391-394 (Exhibit 5).
Cole L.A., P.E. Schwartz and Wang Y. (1988b) Urinary gonadotropin fragments (UGF) in cancers in the female reproductive system. I. Sensitivity and specificity, comparison with other markers. Gynecol. Oncol. 31:82-90 (Exhibit 6).
Cole L.A., Wang Y., Elliot M., Latif M., Chambers J.T., Chambers S.K. and Schwartz P.E. (1988a) Urinary Human Chorionic Gonadotropin Free β-subunit and β-core Fragment: a new marker of gynecological cancer. Cancer Res. 48:1356-1360 (Exhibit 7).
Ehrlich P.H., Moyle W.R., Moustafa Z.A. and Canfield R.E. (1982) Mixing two monoclonal antibodies yields enhanced affinity for antigen. J. Immunol. 128:2709-2713 (Exhibit 8).
Kovalevskaya G., Birken S., O'Connor J., Schlatterer J., Madelman Y. and Canfield R. (1995) HLH beta core fragment immunoreactivity in the urine of ovulating women: A sensitive and specific immunometric assay for its detection. Endocrine 3: 881-887 (Exhibit 9).
Krichevsky A., Armstrong E.G., Schlatterer J., Birken, S., O'Connor J., Bikel K., Silverberg S., Lustbader J., and Canfield R. (1988) Preparation and characterization of antibodies to the urinary fragment of the human chorionic gonadotropin β-subunit. Endocrinology 123:584-593 (Exhibit 10).

(Continued)

*Primary Examiner*—Larry R. Helms
*Assistant Examiner*—Parithosh K. Tungaturthi
(74) *Attorney, Agent, or Firm*—John P. White; Cooper & Dunham LLP

(57) ABSTRACT

The subject invention provides a method for detecting the presence of human malignant cells in a sample of tumor cells, which comprises contacting the sample with an antibody directed to an epitope present on the β subunit of human luteinizing hormone or on intact human luteinizing hormone under conditions such that the antibody forms a complex with cells present in the sample if the epitope is present on the surface of the cells, and determining whether the antibody forms such a complex. The subject invention also provides a method for determining whether a tumor present in a human subject is malignant which comprises obtaining a sample of cells from the tumor and detecting the presence of malignant cells in the sample according to the method of the subject invention. Finally, the subject invention provides a method for obtaining an enriched population of live human malignant cells which comprises contacting a population of cells comprising live human malignant cells with an antibody directed to an epitope present on the B subunit of human luteinizing hormone or on intact human luteinizing hormone under conditions such that the antibody forms a complex with the cells present in the population if the epitope is present on the surface of the cells, and isolating the cells which form a complex with the antibody.

13 Claims, 3 Drawing Sheets

OTHER PUBLICATIONS

Krichevsky A., Birken S., O'Connor J.F., Bikel K., Schlatterer J.P. and Canfield R.E. (1994) The development of a panel of monoclonal antibodies to human luteinizing hormone and its application to immunological mapping and two-site assays. Endocrine 2: 511-520 (Exhibit 11).

Lee C.L., Iles R.K., Shepherd J.H., Hudson C.N. and Chard T. (1991) The purification and development of a radioimmunoassay for beta-core fragment of human chorionic gonadotrophin in urine: application as a marker of gynaecological cancer in premenopausal and postmenopausal women. J. Endocrinol. 130: 481-489 (Exhibit 12).

Moore G.E., Merrick S.B., Woods L.K. and Arabasz N.M. (1975) A human squamous cell carcinoma cell line. Cancer Research 35:2684-2688 (Exhibit 13).

O'Connor, J.F., Kovalevskaya G., Birken S., Schlatterer J.P., Schechter D., McMahon D.J. and Canfield R.E. (1998) The expression of the urinary forms of human luteinizing hormone beta fragment in various populations as assessed by a specific immunoradiometric assay. Human Reproduction 13: 826-83 (Exhibit 14).

O'Connor J.F., Schlatterer J.P., Birken S., Krichevsky A., Armstrong E.G., McMahon D., Canfield R.E. (1988) Development of highly sensitive immunoassays to measure human chorionic gonadotropin, its β-subunit, and 3-core fragment in urine: application to malignancies. Cancer Res. 48:1361-1366 (Exhibit 15).

Odell W.D., Griffin J. (1987) Two-monoclonal-antibody "Sandwich-type" assay of human lutropin, with no cross reaction with choriogonadotropin. Clin. Chem. 33:1603-1607 (Exhibit 16).

Pierce J. and Parsons T. (1981) Glycoprotein hormones: structure and function. Ann. Rev. Biochem. 50:465-495 (Exhibit 17).

Raikow R.B., Acevedo H.F., Krichevsky A., Buffo M.J. and Fogarty P. (1987)Flow cytofluorometric analyses of choriogonadotropin-like material on the surface of human and mouse malignant cells. Cancer Detect. Prev. (Suppl. 1) H. Nieburgs & J. Bekes, Ed., 173-181 (Exhibit 18).

Rosen S.W., Weintraub B.D. and Aaronson S.A. (1980) Nonrandom ectopic protein production by malignant cells; direct evidence in vitro. J. Clin. Endocrinol. Metab. 50:834-841 (Exhibit 19).

Sorenson G.D., Pettengill O.S., Brinck-Johnsen T., Cate C.C. and Maurer L.H. (1981) Hormone Production by cultures of small-cell carcinoma of the lung. Cancer 47:1289-1296 (Exhibit 20).

\* cited by examiner

Expression of Memebrane associated hLH and hCG by cultured
CCL 227. SW 620 Colon Cancer Cells
P : 95 ; %V. 90 : RPMI 1640, 1% Nutridoma-SP

ANTI-HUMAN LUTEINIZING HORMONE-RELATED ANTIBODIES AND USES THEREOF

The present application is a Continuation of application Ser. No. 08/478,431, Filed on Jun. 7, 1995, now U.S. Pat. No. 6,403,326 which is a Continuation of application Ser. No. 08/062,925, Filed on May 13, 1993 now Abandoned.

This invention was made with support under Grant No. P01 HD 15454 from the National Institutes of Health. Accordingly, the U.S. government has certain rights in the invention.

BACKGROUND OF THE INVENTION

Throughout this application various publications are referenced by Arabic numerals. Full citations for these references may be found at the end of the specification immediately preceding the claims. The disclosure of these publications is hereby incorporated by reference into this application to describe more fully the art to which this invention pertains.

The human glycoprotein gonadotropic hormones—luteinizing hormone (hLH), follicle stimulating hormone (hFSH), and chorionic gonadotropin (hCG)—are essential for reproduction. These hormones, along with thyroid stimulating hormone (hTSH), are composed of a common alpha subunit noncovalently combined with a target-specific beta subunit (1, 2) and they appear in blood and urine in a variety of forms ranging from the heterodimeric intact molecules to small fragments (1, 2). All of the glycoprotein hormones are produced by the pituitary, including a small quantity of human chorionic gonadotropin (3).

hLH is known to exist intracellularly, and also in soluble, extracellular form. However, hLH has not been known to exist on the surface of cells. Data presented herein demonstrate the existence of hLH on the surface of human malignant cells.

Certain methods of detecting malignant cells currently exist. However, these methods are generally expensive and time consuming. Accordingly, there exists a need for a rapid and relatively inexpensive method for detecting human malignant cells.

The subject invention provides a method for detecting the presence of human malignant cells in a sample of tumor cells, as well as a method for determining whether a tumor present in a human subject is malignant, which methods exploit the existence of hLH on the surface of malignant cells.

The subject invention further provides a method for obtaining an enriched population of live human malignant cells, which method also exploits the existence of hLH on the surface of malignant cells.

SUMMARY OF THE INVENTION

The subject invention provides a method for detecting the presence of human malignant cells in a sample of tumor cells, which comprises contacting the sample with an antibody directed to an epitope present on the β subunit of human luteinizing hormone or on intact human luteinizing hormone under conditions such that the antibody forms a complex with cells present in the sample if the epitope is present on the surface of the cells, and determining whether the antibody forms such a complex so as to thereby detect the presence of human malignant cells in the sample.

In one embodiment, the antibody is a monoclonal antibody. The monoclonal antibody may be the monoclonal antibody designated B406, B408, B413 or B409. The hybridoma cell lines producing these antibodies were deposited on Nov. 6, 2001 pursuant to the requirements of the Budapest Treaty on the International Recognition of the Deposit of Microorganisms for the Purposes of Patent Procedure with the American Type Culture Collection (ATCC), 10801 University Boulevard, Manassas, Va. 20110-2209, under ATCC Designation Nos. PTA-3832, PTA-3833, PTA-3834 and PTA-3835, respectively.

The subject invention also provides a method for determining whether a tumor present in a human subject is malignant which comprises obtaining a sample of cells from the tumor and detecting the presence of malignant cells in the sample according to the method of the subject invention so as to thereby determine whether the tumor is malignant.

Finally, the subject invention provides a method for obtaining an enriched population of live human malignant cells which comprises contacting a population of cells comprising live human malignant cells with an antibody directed to an epitope present on the β subunit of human luteinizing hormone or on intact human luteinizing hormone under conditions such that the antibody forms a complex with the cells present in the population if the epitope is present on the surface of the cells, and isolating the cells which form a complex with the antibody so as to obtain an enriched population of live human malignant cells.

In one embodiment, the antibody is a monoclonal antibody. The monoclonal antibody may be the monoclonal antibody designated B406, B408, B413 or B409.

Figure 1:
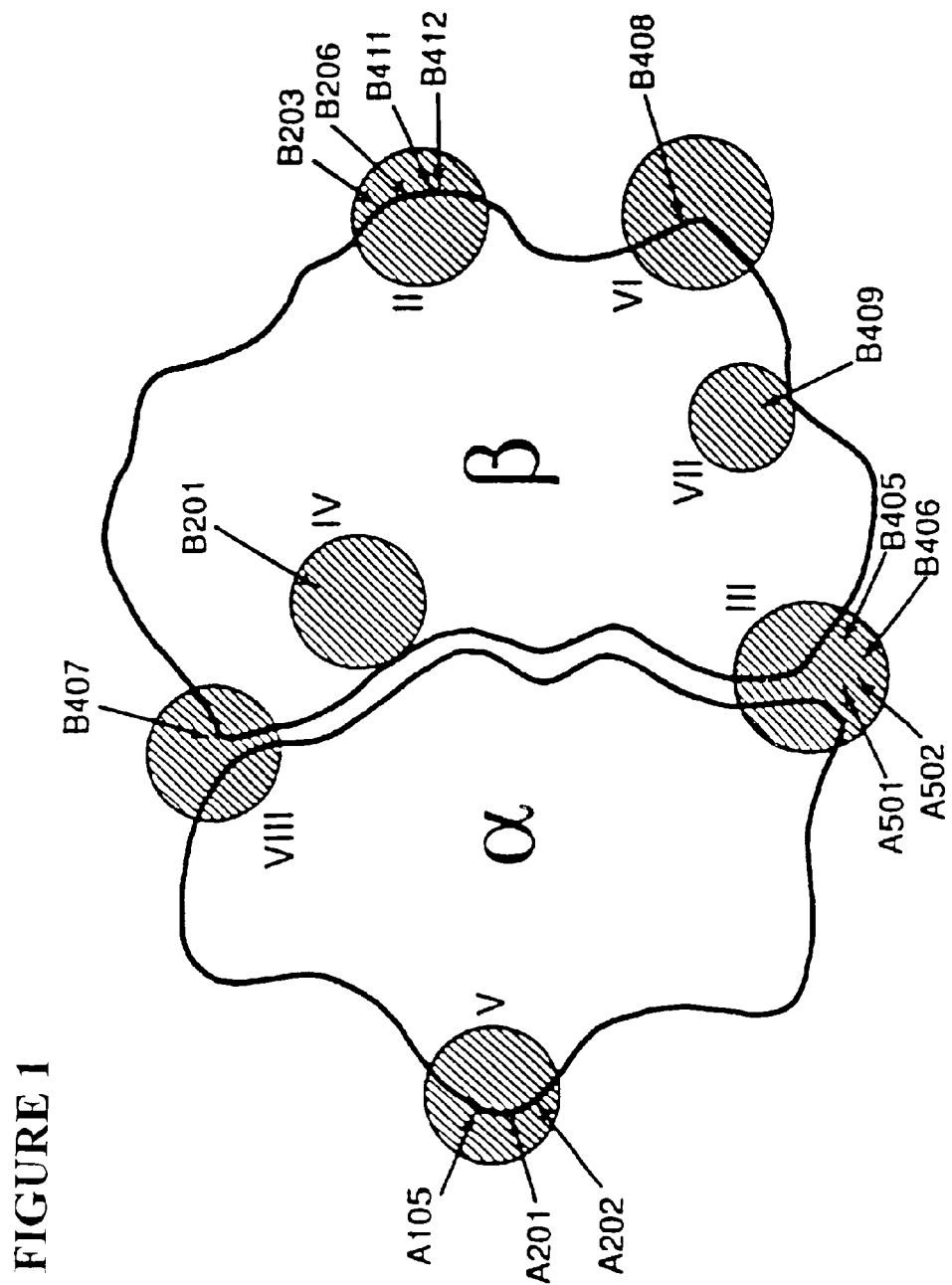
FIG. 1

Epitope binding for antibodies to hLH. The relative locations of seven antibody-binding regions (cross-hatched circles enumerated by Roman numerals) based upon the ability of antibodies to bind simultaneously (different sites) or inhibit each other from binding (same sites). Details of the site assignments are described infra. The numbering of sites starts from Site II because Site I was used earlier to designate the COOH-terminal-related binding region on hCG (5, 12). This region is absent from hLH.

FIG. 2

Expression of membrane-associated hLH and hCG by cultured CCL 227, SW 620 colon cancer cells. P:93; % V:90; RPMI 1640, 1% Nutridoma-SP.

DETAILED DESCRIPTION OF THE INVENTION

Specifically, the subject invention provides a method for detecting the presence of human malignant cells in a sample of tumor cells, which comprises contacting the sample with an antibody directed to an epitope present on the β subunit of human luteinizing hormone or on intact human luteinizing hormone under conditions such that the antibody forms a complex with cells present in the sample if the epitope is present on the surface of the cells, and determining whether the antibody forms such a complex so as to thereby detect the presence of human malignant cells in the sample.

As used herein, "malignant" means capable of metastasizing. As used herein, "tumor cells" are cells which originate from a tumor, i.e., from a new growth of different or abnormal tissue. The tumor cells may exist as part of the tumor mass, or may exist as free-floating cells detached from the tumor mass from which they originate.

As used herein, the term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof.

As used herein, an "epitope present on intact human luteinizing hormone" means an epitope which is formed by the juxtaposition of the α and β subunits of human luteinizing hormone, and which exists only on the intact human luteinizing hormone comprising the α and β subunits. With respect to hLH bound to the surface of malignant cells, epitopes present on the β subunit and on the intact hormone are exposed to the extracellular medium, and hence are able to bind to antibodies directed thereto.

"Conditions such that the antibody forms a complex with cells present in the sample" are well known to those skilled in the art.

"Determining" whether the antibody forms such a complex may be accomplished according to methods well known to those skilled in the art. In the preferred embodiment, determining is accomplished according to the flow cytometry methods described, infra.

In one embodiment, the antibody is a monoclonal antibody. The monoclonal antibody may be the monoclonal antibody designated B406, B408, B413 or B409. The monoclonal antibodies designated B406, B408 and B409 are also referred to herein as KB12, KB21 and KB31, respectively.

The subject invention also provides a method for determining whether a tumor present in a human subject is malignant which comprises obtaining a sample of cells from the tumor and detecting the presence of malignant cells in the sample according to the method of the subject invention so as to thereby determine whether the tumor is malignant.

Obtaining a sample of cells from the tumor may be accomplished using methods well known to those skilled in the art.

Finally, the subject invention provides a method for obtaining an enriched population of live human malignant cells which comprises contacting a population of cells comprising live human malignant cells with an antibody directed to an epitope present on the β subunit of human luteinizing hormone or on intact human luteinizing hormone under conditions such that the antibody forms a complex with the cells present in the population if the epitope is present on the surface of the cells, and isolating the cells which form a complex with the antibody so as to obtain an enriched population of live human malignant cells.

As used herein, an "enriched population of live human malignant cells" is a population of cells, wherein the percentage of cells being live human malignant cells is greater than the percentage of cells being live human malignant cells in the population of cells contacted with the antibody. For example, assume 10% of cell population A are live human malignant cells. Cell population A is contacted with an antibody directed to an epitope present on the β subunit of human luteinizing hormone or on intact human luteinizing hormone according to the method of the subject invention. Cells forming a complex with the antibody are isolated, and the isolated cells form cell population B. If greater than 10% of cell population B are live human malignant cells, then cell population B is an "enriched population of live human malignant cells."

In one embodiment, the antibody is a monoclonal antibody. The monoclonal antibody may be the monoclonal antibody designated B406, B408, B413 or B409.

The antibody may be bound to an insoluble matrix such as that used in affinity chromatography. As used in the subject invention, isolating the cells which form a complex with the immobilized monoclonal antibody may be achieved by standard methods well known to those skilled in the art. For example, isolating may comprise affinity chromatography using immobilized antibody.

Alternatively, the antibody may be a free antibody. In this case, isolating may comprise cell sorting using free, labeled primary or secondary antibody. Such cell sorting methods are standard and are well known to those skilled in the art.

This invention will be better understood by reference to the Experimental Details which follow, but those skilled in the art will readily appreciate that the specific experiments detailed are presented in order to illustrate, and in no way limit, the invention as described more fully in the claims which follow thereafter.

Experimental Details

I—Development and Characterization of Monoclonal Antibodies to Human Luteinizing Hormone A. Introduction The relative binding properties of antibodies directed to hLH and of similar antibodies developed earlier to hCG were ascertained, and evidence was found for at least seven different binding sites on hLH, of which sites three are also present on hCG.

Studies were initiated to develop and characterize a series of monoclonal antibodies designed such that two or more of them would bind simultaneously to the surface of the intact hormone, its subunits, or fragments. Specific measuring systems for hLH depend on the highly successful IRMA (immunoradiometric assay) format of capture and detection antibody pairs which bind simultaneously to different portions of the molecule being measured (4, 6, 7, 11, 12). The development and characterization of a library of high affinity hLH monoclonal antibodies is reported herein, and a topological map defining different antibody binding regions is provided.

B. Materials and Methods

Preparation of Immunogens, Immunization Methods and Selection of Animals

Intact hLH (NPA Lot #AFP827013) was used for immunization at a dose of 30 μg of hLH per mouse. The hormone was diluted in saline and emulsified 1:1 with complete Freund's adjuvant (Calbiochem, San Diego, Calif.). hCGα subunit was conjugated to bovine thyroglobulin as described previously (5) and used for immunization of mice at a dose of 5 μg of hCGα subunit, in conjugated form, per mouse. This immunogen was also diluted in saline and mixed 1:1 with complete Freund's adjuvant. Initial immunization and subsequent boosts were done by IP injections. The mice were boosted twice with the same dose of immunogen at 4–5 week intervals. Nine days after the last boost injection, mice were bled and serum antibody levels to hLH and hCGα were determined by liquid phase double antibody RIA (12). At this stage, the spleen of one of the mice immunized with hLH, whose serum displayed good binding of radiolabeled hLH, was used for fusion. The other mice were boosted at 8-week intervals for another 8 months. The spleen from one mouse immunized with hLH and the spleen from a second mouse immunized with the hCGα subunit were each separately used for two fusions designated "hLH fusion" and the "hCGα fusion", respectively.

Fusion and Selection of Cell Lines for Cloning

The mice used for both hLH fusions were given booster injections intravenously with 75 μg of intact hLH 72 hours before fusion. The mouse used for the "hCGα fusion" was boosted with 20 μg of hCGα conjugate in the same manner. A detailed protocol for production of hybridoma cell lines has been reported earlier (5) and it was used without modification. Approximately 90% of the wells seeded with fusion products exhibited cell growth. Supernates from these wells were assayed by RIA (12) for the presence of antibodies against hLH, hLHβ, hCG, and hCGα in the "hLH fusion", and hCGα and hCG antibodies from the "hCGα fusion" were tested for the ability to bind simultaneously with the previously reported A109 antibody (12) to free α subunit as described (12). Cells growing in wells whose supernates bound selected tracers were propagated until they reached a density of $3\times10^7$ to $5\times10^7$. At this time, cells were frozen in liquid nitrogen and the supernates saved for further testing. Supernates were tested for antibodies which could bind to highly purified preparations of hLH, hLHβ, hCG, and hCGα, both in liquid phase RIA and in solid phase cooperative RIAs, and either simultaneously with already existing antibodies or at the same time with each other. Cloning of selected cells was performed by the limiting dilution method with enough subclonings to insure monoclonality (13). Antibody affinities were determined by the method of Scatchard (14).

IRMA for Intact hLH

Construction of immunoradiometric assays (IRMAS) and characterization of their specificity and sensitivity was described previously (6). Briefly, microtiter wells (Immulon II, Dynatech Laboratories, Inc.) were coated with 200 µl of a 12 µg/ml solution of B406 in 0.2M carbonate buffer, pH 9.5. After overnight incubation at 4° C., the coating antibody solution was aspirated, the wells washed (4x) with wash solution (0.15M NaCl+0.05% Tween-20), and blocked with a 1% bovine serum albumin solution (with 0.1% NaN₃) for 3 hours at room temperature or overnight at 4° C. The BSA solution was aspirated and 200 µl of hLH standard covering a range of 0.098–50 ng/ml hLH and controls in assay buffer (0.01M NaHPO₄, 0.15M NaCl, 0.01M EDTA, 0.1% NaN₃, 0.1% bovine gamma globulin, pH 7.4) were added in duplicate to the wells. The plates were covered with a plate sealer and incubated overnight at room temperature. The wells were then aspirated, washed (6 times) with wash solution, and approximately 100,000 cpm of radiolabeled A201 in 200 µl of buffer was added to each well. Incubation was again carried out overnight at room temperature. The tracer solution was aspirated and the wells washed (6 times) with wash solution. The wells were placed in 12×75 mm glass tubes and counted in a gamma counter. Doses were interpolated from a spline fit of the count data. The least detectable dose was defined as +3SD from multiple replicates of the NSB tubes.

The assay for hLH-free β subunit was essentially identical with the exception of the identities of the antibodies employed.

C. Results

Selection and Characteristics of Antibodies to hLH

The library of antibodies to hLH was selected by identifying the cells from each antibody-producing fusion which reacted uniquely to hLH, while also screening for pairs of antibodies capable of binding to hLH simultaneously.

Cells from the fusions of an hLH-immunized mouse spleen were grown in 96-well tissue culture plates and the supernates were screened for specific binding properties to radiolabeled hLH, hLH β, hCG and hCGα. Initially, there were 61 wells positive with at least one of the tracers employed. Ten of these wells subsequently lost binding activity. This represents an attrition rate of 16%. It was not surprising that the majority of remaining supernates contained antibodies binding intact hLH only (42%), since intact hLH was the immunogen (see Table I).

TABLE I

INITIAL CHARACTERIZATION OF SUPERNATANTS FROM WELLS EXHIBITING BINDING TO DIFFERENT TRACERS

| Tracer | Number of Positive Wells | % of Total Antibody Producing Wells |
| --- | --- | --- |
| hLH | 25 | 41.7 |
| hLHβ | 4 | 6.6 |
| hLH/hLHβ | 13 | 21.7 |
| hLH/hCG | 5 | 8.3 |
| hLH, hLHβ hCG, hCGα | 2 | 3.3 |
| hLH, hCG, hCGα | 1 | 1.7 |
| hLH/hCGα | 1 | 1.7 |
| hCGα | 9 | 15.0 |
| Total | 60 | 100% |

A significant proportion of the wells contained cells producing antibodies to both intact hLH and to its beta subunit (22%), 15% bound only to alpha, and 7% contained antibodies that bound to only the hLH beta subunit. The presence of antibodies directed solely to the free subunits was unexpected since the hLH immunogen appeared to be intact (i.e., there were no free subunits, fragments of peptide bond cleavages) as determined by gel electrophoresis and amino acid sequence analysis (data not shown). Two wells produced antibodies which bound all of the tracers employed. One antibody recognized intact hLH, hCG, and alpha subunit. The other antibody recognized intact hLH and alpha subunit. These results indicate that an extensive panel of antibodies to intact hLH, as well as to its subunits, can be obtained by immunization with this preparation of intact hLH.

The cloned antibodies were grouped based on their simultaneous binding capabilities and on their binding patterns to labeled tracers in liquid and solid phase systems (Table II). The nomenclature of these binding sites is consistent with the format developed for previously reported antibodies to hCG (5) which is based on simultaneous binding of pairs of antibodies or mutual inhibition in liquid and solid phase assays. For example, antibodies designated as directed to the same site will not bind to the hormone or subunits simultaneously, while those directed to different sites will bind at the same time. By the use of the simultaneous binding and inhibition of binding criteria, it was possible to map the antibodies described herein to seven different epitopes on hLH (FIG. 1). Some of these binding sites are shared with hCG while others are unique to hLH.

TABLE II

SUMMARY OF SPECIFICITIES AND BINDING CHARACTERISTICS OF MONOCLONAL ANTIBODIES IN LIQUID AND SOLID PHASE IMMUNOASSAYS

| BINDING SITE ON EPITOPE MAP | ANTIBODY (ISOTYPE) | ANTIBODY BINDS TO THE FOLLOWING ANTIGENS IN LIQUID PHASE R1A | | | | | ANTIBODY BINDS SIMULTANEOUSLY WITH ANTIBODIES IN SOLID PHASE ASSAY | ANTIBODY CANNOT BIND SIMULTANEOUSLY WITH ANTIBODIES IN SOLID PHASE ASSAY |
| --- | --- | --- | --- | --- | --- | --- | --- | --- |
| | | hLH | hCG | hLHβ | hCGβ | hCGα | | |
| II | B-411 (IgG1) | 100% | 60% | 120% | 60% | ND | B201, A105, B207, A501, B409 | B203, B206 |

TABLE II-continued

SUMMARY OF SPECIFICITIES AND BINDING CHARACTERISTICS OF MONOCLONAL
ANTIBODIES IN LIQUID AND SOLID PHASE IMMUNOASSAYS

| BINDING SITE ON EPITOPE MAP | ANTIBODY (ISOTYPE) | ANTIBODY BINDS TO THE FOLLOWING ANTIGENS IN LIQUID PHASE RIA | | | | | ANTIBODY BINDS SIMULTANEOUSLY WITH ANTIBODIES IN SOLID PHASE ASSAY | ANTIBODY CANNOT BIND SIMULTANEOUSLY WITH ANTIBODIES IN SOLID PHASE ASSAY |
|---|---|---|---|---|---|---|---|---|
| | | hLH | hCG | hLHβ | hCGβ | hCGα | | |
| II | B412 (IgGA) | 100% | 80% | 300% | 200% | ND | A105, A201, A202, A501, A502 | B203, B206, B207 |
| II | B207 (IgG1) | 100% | NT | 1000% | NT | ND | A105, A201, A202, B408, A501, A502, B201, B407, B405, B406, B411, B409 | B203, B206, |
| III | B405 (IgG2a) | 100% | ND | ND | ND | ND | A105, A201, A202, B203, B206, B207, B411 | B406, A501, A502, B201 |
| III | B406 (IgG2a) | 100% | ND | ND | ND | ND | A105, A201, A202, B203, B206, B207, B411 | B405, A501, A502, B201, |
| IIIa | A501 (IgG1) | 3% | 0.7 | ND | ND | 100% | A105, A201, A202, B203, B206, B207, B411 | B409, B405, B201, B406, A502, B408, |
| IIIa | A502 (IgG1) | 0.1% | .2% | ND | ND | 100% | A105, A201, A202, B203, B206 B207, B411 | B409, B405, B203, B406, A501, B409 |
| V | A201 (IgG1) | NT | 7.5% | ND | NT | 100% | B203, B206, B207, A501, A502, B407, B411 | A105, A202, B409, |
| V | A202 (IgG1) | NT | 40% | ND | NT | 100% | B206, B207, B405, B406, A501, A502, A201 | A105, A201, B409 |
| VI | B408 (IgG1) | 100% | ND | 830% | ND | ND | B203, B206, B207, B209, B407, B409 | B405, B406, A501, A502, B201, A105 |
| VII | B409 (IgG1) | ND | ND | 100% | ND | ND | B203, B206, B207, B408, B201, B411, A105, A201 | B405, B406, A501, A502, |
| VIII | B407 (IgG1) | 100% | 100% | ND | ND | ND | B203, B206, B207, B405, B406, A501, A502, A105, A201, A202 | B409, B411 |

NT = NOT TESTED
ND = NONE DETECTABLE

Table II starts with Site II antibodies since the Site I type is associated with the unique beta subunit COOH-terminal epitope on hCG and is not present on hLH. The characteristics of each of these new antibodies to hLH appear in Table II. Also included in Table II are the characteristics of several antibodies developed to the hCG beta fragment which also bind to hLH. These antibodies were used to construct the IRMA systems described supra. The affinities for each of these antibodies to hCG and hLH, as well as their subunits, appear in Table III. The data for other antibodies have been reported previously (5).

Four antibodies to Site II, which is present on both hLH and hCG, are listed in Tables II and III. Two are developed from mice immunized with hLH (B411 and B412) and two (B203 and B206) are from mice immunized with the hCG beta fragments (5). All four display the same specificity profile. Each binds to intact hLH, hCG, hCG beta and hLH beta as well as to the hCG beta fragment, but not to the alpha subunit. None of these antibodies bind to labelled FSH. Two antibodies were developed from mice immunized with hLH (B411 and B412) and both have similar affinities to hCG and hLH in the range of $10^9$ to $10^{10}$ L/M (Table III).

Site III antibodies fall into two categories. This is indicated by segmentation of the Site as III and IIIa on Table II. Two antibodies, B405 and B406, bind only to hLH in both liquid and solid phase systems (Table II) with affinities of $10^7$ and $10^8$ L/M, respectively (Table III), and are designated as Site III types. Two other antibodies (A501 and A502) listed as Site IIIa

TABLE III

RELATIVE AFFINITIES (LITER PER MOLE) OF hLH, hCG, hCGβ and hCGα FOR EACH OF THE REPORTED ANTIBODIES

| Antibody | Tracer | COMPETITORS | | | | |
|---|---|---|---|---|---|---|
| | | hLH | hCG | hLHβ | hCGβ | hCGα |
| B411 | hLH | $5 \times 10^9$ | $3 \times 10^9$ | $3 \times 10^9$ | $2 \times 10^9$ | ND |
| | hLHβ | $3 \times 10$ | $3 \times 10^9$ | $6 \times 10^9$ | $3 \times 10^9$ | ND |
| | hCG | NT | $3 \times 10^9$ | NT | $1 \times 10^9$ | ND |
| | hCGβ | NT | NT | NT | $3 \times 10^9$ | ND |
| B412 | hLH | $1 \times 10^{10}$ | NT | $3 \times 10^{10}$ | NT | NT |
| | hLHβ | $2 \times 10^{10}$ | NT | $3 \times 10^{10}$ | NT | NT |
| | hCG | $2 \times 10^{10}$ | $3 \times 10^9$ | $1 \times 10^{10}$ | $2 \times 10^{10}$ | NT |
| | hCGβ | $3 \times 10^9$ | $7 \times 10^9$ | $6 \times 10^9$ | $6 \times 10^9$ | NT |
| B405 | hLH | $8 \times 10^7$ | ND | ND | ND | ND |
| B406 | hLH | $8 \times 10^8$ | ND | ND | ND | ND |
| A501 | hCG | NT | $4 \times 10^7$ | ND | ND | NT |
| | hLH | $2 \times 10^8$ | NT | NT | NT | NT |
| | hCGα | NT | $3 \times 10^7$ | ND | ND | $6 \times 10^8$ |
| A502 | hCG | ND | ND | ND | ND | ND |
| | hLH | $5 \times 10^8$ | NT | ND | ND | NT |
| | hCGα | NT | $1 \times 10^7$ | ND | ND | $5 \times 10^9$ |
| A201 | hCGα | NT | $3 \times 10^7$ | ND | NT | $4 \times 10^8$ |
| A202 | hCGα | NT | $4 \times 10^7$ | ND | NT | $1 \times 10^8$ |
| B408 | hLH | $7 \times 10^9$ | ND | $2 \times 10^{10}$ | ND | ND |
| | hLHβ | NT | ND | $6 \times 10^{10}$ | ND | ND |
| B409 | hLH | ND | ND | ND | ND | NT |
| | hLHβ | ND | ND | $3 \times 10^9$ | ND | NT |
| | hCG | ND | ND | ND | ND | NT |
| | hCGβ | ND | ND | ND | ND | NT |
| B407 | hLH | $2 \times 10^8$ | NT | NT | NT | ND |
| | hCG | NT | $2 \times 10^8$ | NT | NT | ND |

ND = Non-detectable
NT = Not tested antibodies, bind weakly to intact hLH but strongly to free alpha subunit (Table III). Although they cannot bind simultaneously with other class III antibodies, they do bind simultaneously with region V antibodies to the a subunit, so they are obviously directed to a close but distinct region of the hormone and are thus designated as belonging to Site IIIa.

One antibody developed earlier to a fragment of the hCG beta subunit, B201 (5), is listed in class IV and binds only to the beta subunits of hLH and hCG with an affinity of $10^{10}$ L/M. This is the first report of such an hLH-free beta subunit antibody that discriminates subunit from the intact heterodimer.

There are three Site V antibodies listed which bind both intact hLH and its free alpha subunit. One antibody, developed to intact hCG, A105, was reported earlier (5). The other two antibodies, A201 and A202, were developed to the alpha subunit using hCG alpha as the immunogen. Antibodies from these cell lines displayed better binding to radiolabeled hCG alpha subunit than to labelled intact hCG in liquid phase assays (Table III). These two antibodies, A201 and A202, were selected for their ability to bind simultaneously with antibody A109 (a Site III antibody) (12) to alpha subunit (see Materials and Methods, this section). Antibodies A201 and A202 bind simultaneously with A109, A501 and A502 to free alpha subunit (Table II). These new antibodies led to IRMA assays for intact hLH that are superior to those using the earlier developed antibody, A105 (see Table IV and the text below).

TABLE IV

Sensitivities (minimal detectable doses) in pmoles/ml of IRMA systems

| Capture Antibody Concentration | Antigen | B203 | B206 | B411 | B405 | B406 | A501 | A502 | B201 | A105 | A201 | B409 | B407 |
|---|---|---|---|---|---|---|---|---|---|---|---|---|---|
| B203 (5 µg/well) | βhCG | — | a | a | a | a | a | a | 0.20 | a | NT | 0.20 | a |
| | hCG | — | 0.7 | a | a | a | 0.2 | 0.3 | a | 0.02 | NT | 1.70 | 0.02 |
| | hLH | — | 0.7 | a | 0.03 | 0.05 | 0.3 | 0.6 | a | 0.80 | NT | 0.20 | 0.01 |
| | βhLH | — | 1.5 | a | a | a | a | a | 1.5 | a | NT | 0.02 | a |
| B206 (5.8 µg/well) | βhCG | a | — | a | a | a | a | a | 0.10 | a | NT | 1.0 | a |
| | hCG | a | — | a | a | a | 0.4 | 0.30 | a | 0.03 | NT | 2.1 | 0.02 |
| | hLH | a | — | a | 0.03 | 0.05 | 0.3 | 0.50 | a | 0.30 | NT | 0.11 | 0.01 |
| | hLH | a | — | a | 1.70 | a | a | a | 1.0 | a | NT | 0.03 | 2.0 |
| B411 (2.6 µg/well) | βhCG | a | a | — | a | a | 0.60 | a | 0.01 | a | a | 0.30 | a |
| | hCG | a | a | — | a | a | 0.05 | 0.08 | 0.13 | 0.085 | 0.021 | a | 0.01 |
| | hLH | a | a | — | 0.01 | 0.006 | 0.07 | 0.21 | 0.35 | 0.208 | 0.013 | 0.10 | 0.006 |
| | βhLH | a | 1.4 | — | 0.69 | 0.347 | a | a | 0.05 | a | a | 0.01 | a |
| B405 (2.6 µg/well) | βhC2 | a | a | a | — | a | a | a | a | a | a | a | a |
| | hC2 | a | a | a | — | a | a | a | a | a | a | a | a |
| | hL4 | 0.02 | 0.05 | a | — | a | a | a | a | 0.01 | 0.05 | a | 0.052 |
| | βhL4 | 1.7 | 0.7 | a | — | a | a | a | a | a | a | a | a |
| B406 (5.0 µg/well) | βhC2 | a | a | a | a | — | a | a | a | a | a | a | a |
| | hC3 | a | a | a | a | — | a | a | a | a | a | a | a |
| | hL4 | 0.02 | 0.05 | a | a | — | a | a | a | 0.028 | 0.007 | a | 0.052 |
| | βhLH | 1.4 | 1.4 | a | a | — | a | a | a | a | a | a | a |
| A501 (9 µg/well) | hC2 | 0.6 | 0.2 | a | a | a | — | a | a | 0.05 | 0.011 | a | 1.36 |
| | hLH | 0.2 | 0.5 | a | a | a | — | a | a | 0.02 | 0.013 | a | 0.83 |
| | αhCG | a | a | a | a | a | — | a | a | 0.005 | 0.005 | a | a |
| A502 (9.4 µg/well) | hCG | 0.5 | 0.08 | a | a | a | a | — | a | 0.05 | 0.043 | a | 0.68 |
| | hLH | 0.1 | 0.1 | a | a | a | a | — | a | 0.03 | 0.026 | 0.4 | 0.83 |
| | hCG | a | a | a | a | a | a | — | a | 0.02 | 0.005 | a | a |
| B201 (4 µg/well) | βhCG | 0.1 | 0.05 | 0.05 | a | a | a | 2.3 | — | a | NT | 0.25 | NT |
| | hCG | 2.0 | 0.4 | 0.45 | a | a | a | a | — | a | NT | 1.7 | NT |
| | hLH | 0.8 | 0.3 | 0.45 | a | a | a | a | — | a | NT | 0.1 | NT |
| | βhLH | 0.1 | 0.08 | 0.14 | a | a | a | a | — | a | NT | 0.02 | NT |
| A105 (5 µg/well) | hCG | 0.05 | 0.02 | 0.68 | a | a | 0.17 | a | a | — | NT | a | 0.085 |
| | hLH | 0.15 | 0.20 | 1.67 | 0.01 | 0.01 | 0.03 | 0.83 | a | — | NT | a | 0.013 |
| | αhCH | a | a | a | a | a | 0.001 | 0.02 | a | — | NT | a | a |
| A201 (5 µg/well) | hCG | 0.05 | 0.02 | a | a | a | 0.085 | 0.043 | NT | a | — | a | 0.043 |
| | hLH | 0.05 | 0.08 | a | 0.01 | 0.013 | 0.026 | 0.013 | NT | a | — | a | 0.013 |
| | αhCG | a | a | a | a | a | 0.003 | 0.003 | NT | a | — | a | 0.862 |
| A202 (10 µg/well) | hCG | NT | 0.02 | NT | a | a | 0.042 | 0.043 | NT | a | NT | a | NT |
| | hLH | NT | 0.06 | NT | 0.01 | 0.006 | 0.026 | 0.013 | NT | a | NT | a | NT |
| | αhCG | NT | 0.7 | NT | a | a | 0.003 | 0.003 | NT | a | NT | a | NT |
| B409 (15.6 µg/well) | βhCG | 0.06 | 0.02 | a | a | a | a | a | 0.2 | a | a | — | a |
| | hCG | 1.80 | a | a | a | a | a | a | 1.5 | a | a | — | a |
| | hLH | 0.10 | 0.1 | a | a | a | a | a | 1.7 | a | a | — | a |
| | βhLH | 0.02 | 0.04 | a | a | a | a | a | 0.08 | a | a | — | a |
| B408 (16 µg/well) | βhCG | a | a | a | a | a | a | a | a | a | a | a | a |
| | hCG | a | a | a | a | a | a | a | a | a | a | a | a |
| | hLH | 0.01 | 0.05 | a | a | a | a | a | a | 0.1 | 0.01 | a | 0.052 |
| | βhLH | 0.01 | 0.01 | a | a | a | a | a | a | a | 0.01 | a | a |
| B407 | βhCG | a | a | a | a | a | a | a | a | a | a | a | — |

One antibody each is assigned to separate binding Sites VI, VII and VIII. These are: B408, which binds only to hLH beta in liquid phase RIA (Site VI); B409, which binds hLH and its beta subunit but not to hCG or hCG beta and is thus an hLH-specific type of antibody (Site VII); and B407, which binds to intact hCG and hLH but to neither of their free subunits (site VIII). The latter antibody selects for intact dimeric hCG or hLH from mixtures containing both intact hormones and their free subunits and fragments. B407 is the only antibody in the library which binds simultaneously with all of the other antibodies binding to intact hormone species. It was therefore assigned a unique binding site, Site VIII (FIG. 1).

Assessment of Simultaneous Antibody Binding for Assay Development

Table IV represents a summary of studies of the various possible IRMA systems showing the minimal detectable concentrations of hormones or subunits which can be measured by various permutations of capture and detection antibodies. This Table also indicates simultaneous binding as well as competitive binding of the various antibodies. Each capture antibody was coated on Immulon-2 plates to extract antigens from the sample solution. Radiolabeled detection antibodies were used to measure the total antigen bound to the capture antibody. Only detection antibodies capable of binding to an accessible epitope on the captured antigen gave a signal. Two antibodies, B408 and A202, could not be used as detection antibodies since they lost binding capacities after radiolabeling.

The data shown in Table IV, along with data from earlier studies (5) and the results of liquid phase assays (data not shown), were used to produce the epitope map of hLH (FIG. 1). Capture antibodies appear along the left column while radiolabeled detection antibodies appear across the top of Table IV. The types of assays which can be developed using antibodies from each of the assigned binding sites are described infra.

Antibodies to Site II

None of the Site II antibodies exhibit sufficient specificity to be used to capture hLH or its beta subunit from solution, because they bind to both intact hormones and subunits. They can be used in assays to measure total hCG/hLH-related immunoreactive materials in combination with either B201 or B407 as the detection antibody.

Antibodies to Site III

B405 and B406 are useful as capture antibodies to extract intact hLH from solutions. A201 or B407 may be used as the detection antibody to develop assays for intact hLH at sensitivities of 7 fmoles/ml. Site IIIa antibodies (see Tables II and IV) may be used to measure free alpha concentrations when used together with antibodies to Site V. For example, an assay composed of A105 (Site V) as capture antibody and A501 as the labeled tracer antibody results in an assay which will detect free alpha subunit at a sensitivity of 1 fmole/ml.

Antibodies to Site IV

B201 is the only antibody in our library that recognizes free beta hLH and beta fragment and not intact hormone. It is not useful as a capture antibody since it will extract both the beta subunit and beta fragments of hCG and hLH, but it is a very useful detection antibody. For example, using B201 as a detection antibody and B409 as capture, hLH beta may be measured with a sensitivity of 80 fmoles/ml.

Antibodies to Site V

Earlier, the use of these antibodies to measure free alpha subunit and intact hLH was described. From the data in Table IV, it became apparent that it would be useful to obtain more antibodies to subsets of this region because different antibodies could be developed from this general area which would have different specificities and sensitivities. When used as capture to measure intact hLH, either A201 or A202 in conjunction with B406 produces a sensitivity of 7 fmole/ml, in comparison with the earlier described A105, which has a sensitivity of only 208 fmoles/ml.

Antibodies to Site VI

B408 was discussed above. It is used in a specific assay for hLH and the hLH beta subunit.

Antibodies to Site VII

B409 binds only to labeled hLH beta subunit in liquid phase RIA. When used as a detection antibody with B408 as the capture antibody, both intact hLH and beta subunit can be measured with sensitivities of 3 fmoles/ml for hLH and 0.5 fmoles for β subunit.

Antibodies to Site VIII

B407 binds simultaneously with all other antibodies (except those that are β subunit specific) listed in Table IV. B407 can be used together with antibodies B405, B406 and B408 for the construction of specific hLH assays with sensitivities of 50 fmoles/ml.

D. Discussion

Measurements of the glycoprotein hormones have greatly benefitted from the advent of monoclonal antibody technology, which has permitted the accurate quantitation of one hormone or fragment with high sensitivity and good specificity even in the presence of much larger quantities of immunologically-related material. This was accomplished by combining the unique specificities of two monoclonal antibodies in two-site immunoassays (2, 5, 6, 7, 10). The general approach used to develop these assays is to assess the specificity and affinity of each individual antibody to a ligand and then to compare individual antibody pairs. If two antibodies can bind to the ligand simultaneously, each antibody is designated as binding to a different site on the ligand. If two antibodies compete for binding to a ligand, they are designated as binding to the same site. This process of determining binding sites on a ligand is termed "immunological mapping." Immunological mapping of these hormones has not only advanced measurement techniques but has helped in understanding the topographical relationships between some major surface features by the use of assays incorporating simultaneous antibody binding. Human chorionic gonadotropin has been most extensively studied in this manner (2). Such mapping has also been performed with the other glycoprotein hormones, hLH (8, 9), hFSH (15), hTSH (9) but to a lesser extent.

The cloning and selection of monoclonal antibodies to hLH was quite different from earlier experiences with hCG antibodies. The majority of antibodies resulting from immunization with hCG were directed to Site II (FIG. 1) on the beta subunit, which is a site present on both free beta subunit and on the dimeric hormone. Other investigators have had a similar experience with hCG (16, 17). Table I illustrates the difference observed with hLH immunization. In this case, most of the antibody-producing cells from the hLH-immunized animal were directed to Site III, intact hLH (41.7%), and not to hLH/hLH beta (21.7%, the Site II antibodies). It was found that less than 6% of the cells produced antibody directed to both free alpha subunit and dimeric hormone (Site V). In contrast, other groups have found much higher percentages of such antibodies. Soos and Siddle (8), who also immunized mice with intact hLH, found that 50% of the cells producing antibody were directed to alpha subunit. Alonso-Whipple et al. (9) also found that 5% of the antibodies to hLH were directed primarily to the alpha subunit. Berger (15) found that over 65% of the antibodies developed to hFSH were directed to the alpha subunit.

As described below, the selection of antibodies to hLH was geared to obtaining a wide array of antibodies which would bind to different regions of the hormone. The first step in this selection process was the screening of antibody-producing lines with a variety of labeled tracers. The second step was the demonstration of the cooperativity effect (11, 12) to select antibodies which would bind simultaneously with another antibody (5). The third step in selection was the examination of cloned lines by the IRMA technique (Table IV) and the identification of antibodies useful for measurement systems and for epitope mapping. This sequence of procedures resulted in the immunological map presented in FIG. 1.

Seven distinct antibody-binding sites were identified on the surface of hLH (FIG. 1). Earlier, using similar strategies to map hCG, only five sites could be identified, of which one was the unique Site I in the beta COOH-terminal region (5, 11). Immunological mapping of hLH by Alonso-Whipple and colleagues found six sites on alpha and two on beta subunits (9). Other investigators have found various numbers of distinctly different sites, the number depending on the technique employed to assess simultaneous binding. For example, using strictly solid-phase rather than a combination of both liquid phase and solid phase screening, Schwartz et al. (16), Soos and Siddle (8) and Norman et al. (17) identified many more sites on each hormone. Solid phase screening alone seems to either create more sites or make overlapping sites appear more distinct than they do in the liquid phase system. The use of both methods of epitope mapping are preferred, as described herein, for a better representation of discrete sites.

Table II and FIG. 1 summarize the different Sites which were found on hLH from these initial studies. Table II is a guide to the nomenclature and Site specificities of the antibodies described herein. Antibody map sites which are coincident with those of hCG are Sites II, V and IIIa. The antibodies to these Sites will bind at the same time as other dimer-directed antibodies and can be used in a single assay which potentially provides greater specificity than can be obtained with the use of one alone. Table II also lists an antibody developed earlier (5) to a fragment of the beta subunit of hCG (B201). This is the only antibody reported in the literature which binds the free beta subunits of both hCG and hLH, but not intact hLH.

Table III indicates the affinities and cross-reactivities of these various antibodies. Most of the antibodies shown are medium to high affinity ($5 \times 10^7$–$5 \times 10^{10}$ L/M), presumably a consequence of the use of liquid phase assays for clonal selection (18).

Table IV summarizes the data from IRMA-type assays which show how different combinations of capture and detection antibodies can be used to measure specifically a variety of antigens present together with immunologically related molecules in complex solutions. The information which can be gleaned from this table appears in the Results section, supra. Some of the most interesting observations derived from this table are as follows.

1. The combination of B408 as capture and B409 as detection antibodies provides a comprehensive assay for intact hormone, beta subunit and potential fragments of the beta subunit suitable for both urine and serum. B408 captures both intact and beta subunit, while B409 detects both forms with high specificity and sensitivity.
2. The change in specificity of B409 between liquid phase and solid phase assays deserves comment, especially in relation to clonal selection methodology. B409 will recognize only free hLH beta subunit in liquid phase assay, while in the IRMA format it recognized hCG, hCG beta and hLH as either capture or detection antibody. However, it always binds preferentially to hLH beta. There are two kinds of interactions that may alter antibody specificity. A solid phase-bound antibody (capture antibody) may alter presentation of a ligand to a second detection antibody. For example, Rebois showed that the binding of an antibody (generated to native hormone) could change the shape of biologically inactive deglycosylated hormone so that biological activity was restored (19). Alternatively, binding of one antibody to a ligand may cause a distant conformation change in the ligand which alters binding of a second antibody to the ligand. The later effect is exhibited in liquid phase assays or solid phase or both. It is possible that such effects alter the specificity of the antibody, and thus are responsible for the increased cross-reaction with the intact hLH and hCG antigens. Our use of liquid phase screening permitted us to select antibody B409 for cloning. Had we used only a solid phase selection scheme, it would have seemed that this antibody was not at all specific and it would not have been selected for further study (20).

II—Expression of Membrane-Associated Human Luteinizing Hormone by Cultured Human Cancer Cells A. Introduction Cancer cells of different types and origins were grown in serumless medium (Nutridoma) and were analyzed by the flow cytometry method using a highly sensitive MAb directed to a conformational epitope of hLH and MAb against an epitope of hLHβ and hLHβ free. In every case, analysis of hCG and its subunits was also done. According to the results, membrane-associated intact hLH and its subunits are expressed by a variable percent of cells from all the cancer cell lines studied to date. Carcinomas and lymphomas appear to express more intact hLH than sarcomas and retinoblastomas. The amount of hLH and hLHβ that was expressed was always less than the amount of hCG and hCGβ.

B. Materials and Methods

A brief description of the 11 human cancer cell lines used in this study is given in Tables VI and VII. They include 7 carcinomas, 2 sarcomas and single samples of retinoblastoma and burkitt lymphoma. Cells were grown in a humidified incubator at 37° and 5% $CO_2$ in serumless RPMI-1640 or RPMI-1640/DMEN (1:1), and 2 mmol/L L-Glutamine, 1 mmol/L Sodium Pyruvate, 10 MG/L Gentamicin Sulfate and 1% Nutridoma-HU or Nutridoma-SP as a serum replacement. For analysis, all cells were harvested at confluence or near confluence. The flow cytometry method used living cells, a double antibody reaction, a coulter epics C flow cytometer with a 2 W argon laser, standard settings and a filter for fluorescein isothiocyanate, coulter immuno software, the ATCC CCL 2 HeLa cell line as a cell control and for overall quality control for reagent standardization, and a panel of monoclonal antibodies (MAb) directed against a conformational epitope of intact (bioactive, holo) hCG (B109), of intact hLH (KB12 or B413), or hLHβ-total (KB21), of hLHβ free (KB31), of hCGβ-total (AS12), of hCGβ-CTP (AS11) and of the total α-subunit, common for hCG and hLH (A105).

Preparation of Cultured Cells for Flow Cytometry

1. Harvest the cells at confluence, using trypsin 0.25% with ethylenediamine tetraacetic acid 0.1% when necessary, and collect them in a 15-ml or 50-ml tube.
2. Determine the number of cells per ml and the viability using a hemacytometer and trypan blue dye exclusion.
3. Pipette $10^6$ cells into a series of 12×75-mm polypropylene tubes, the number of tubes depending on the number of cells available and the number of antibodies to be used.

4. Pellet the cells by centrifuging at 200×g for 7 minutes and discard the supernatant.
5. Add 100 μl normal goat serum 3% in PBS to each tube and vortex gently for approximately 10–15 seconds. PBS was prepared from a stock solution of PBS 10× concentration (Whittaker, Walkersville, Md.).
6. Incubate the tubes in ice for 30 minutes.
7. Suspend the cells in 3 to 3.5 ml of PBS, vortex gently, and centrifuge suspension at 200×g for 7 minutes. Discard the supernatant.
8. Resuspend the cells in PBS, vortex gently, and centrifuge them at 200×g for 7 minutes. Discard the supernatant.
9. Add each primary antibody to its respective tube, following the plan of the experiment and using appropriate controls.
   a. The protein concentration (mg/ml) of each antibody is determined by the Bradford method (22) using the Bio-Rad protein assay according to the manufacturers instructions.
   b. The amount of antibody in micrograms of protein per $10^6$ cells must be determined experimentally by titration of the antibody with $10^6$ cells of the ATCC CCL 2 HeLa cell contrast.
10. Vortex the tubes gently and briefly.
11. Incubate overnight at 4 to 8° C. on a dimensional rotator.
12. Wash the cells two times with PBS as in steps 7 and 8.
13. Add 100 μl of appropriately diluted fluorescein isothiocyanate-conjugated species-specific second antibody. The concentration of this second antibody must be determined by titration.
14. Vortex the tubes gently and briefly.
15. Incubate in ice for 30 minutes.
16. Wash the cells twice with PBS as in steps 7 and 8.
17. Resuspend the cells in 0.5 ml paraformaldehyde 1% m PBS and vortex each tube gently. The cells can be stored at 4 to 8° C. for one week at this point.
18. Use flow cytometry to determine the percent of cells binding with each antibody.

C. Results and Discussion

Figure 2:
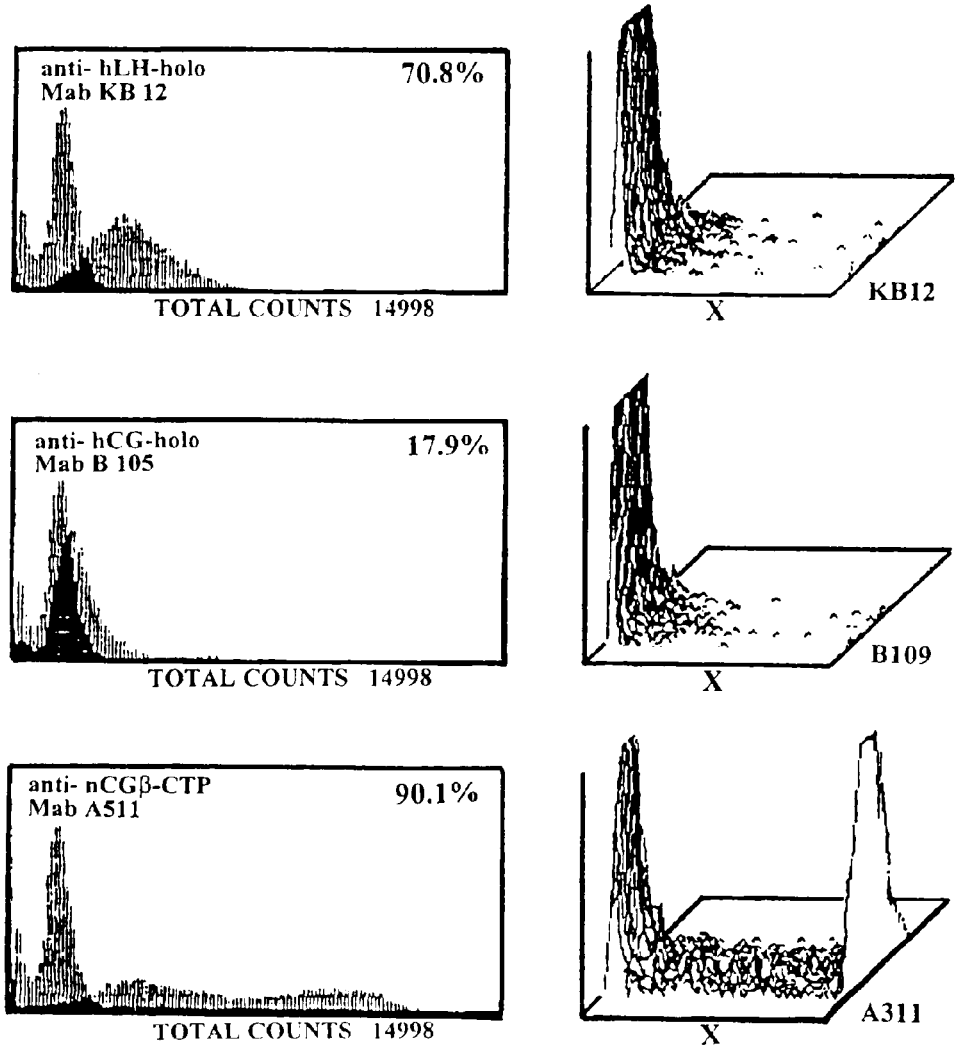
Figure 2:
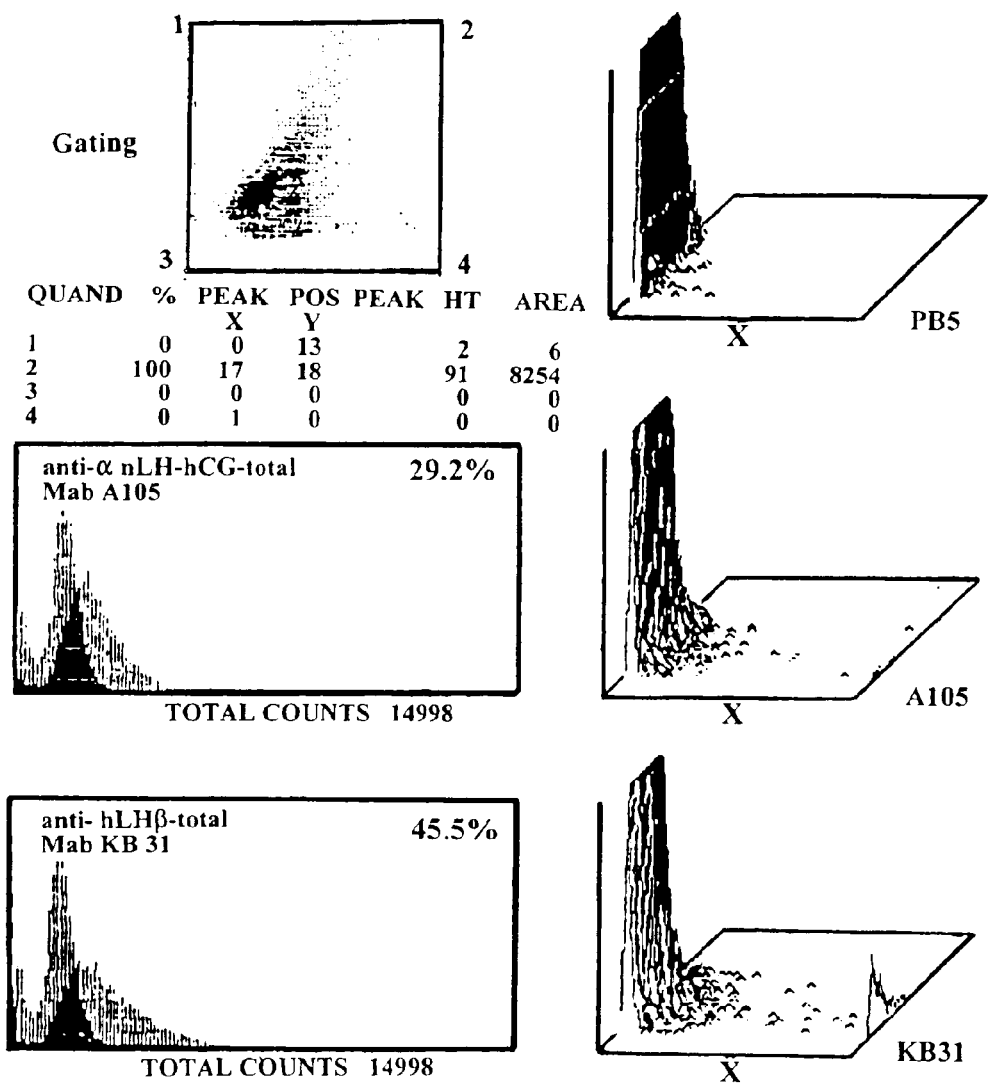

The results shown in Tables V and VI and FIG. 2 demonstrate the following.

1. Membrane-associated hLH and its subunits are expressed by a variable percent of cultured human cancer cells irrespective of type or origin, indicating that the expression of these sialoglycoproteins, like the expression of hCG, its subunits and fragments, is also a phenotypic characteristic of human cancer cells.
2. Since hLHβ is coded by one of the genes of the hCGβ-hLHβ gene cluster, its ectopic expression by cancer cells suggests that the activation of the genes of the hCGβ-hLHβ gene cluster at the molecular level is non-selective.
3. In most instances, in contrast to the case of hCG, most of the expressed material was the complete (bioactive) hLH, suggesting that the hLHβ synthesized by the cancer cells, has a normal tertiary structure.
4. Our results are consistent with the early report of Rosen et al. teaching the presence of low amounts of hLHβ-like material in the cytoplasms, but not in the culture media, of 3 cancer cell lines (21).

TABLE V

EXPRESSION OF MEMBRANE-ASSOCIATED hLH, hCG AND THEIR SUBUNITS AND FRAGMENTS BY CULTURED HUMAN CANCER CELLS.

| Cell line | P# | % V | MAb A105 % α total | MAb KB31 % hLHβ total | MAb KB12 % hLH holo | MAb B109 % hCG holo | MAb AS12 % hCGβ total | MAb AS11 % hCGβ CTP | Cell type | Source |
|---|---|---|---|---|---|---|---|---|---|---|
| HeLa | 113–14 | 84 | 88.5 | 84.8 | 91.1 | 79.9 | NT* | 93.3 | Adenocarcinoma of cervix | ATCC CCL 2 Primary tumor |
| AN3CA | 169 | 87+ | 79.0 | 77.4 | 76.6 | 73.2 | NT | 93.3 | Adenocarcinoma of endometrium | ATCC HTB 111 Primary tumor |
| DU145 | 62 | 94 | 18.8 | 14.4 | 29.3 | 20.4 | NT | 38.8 | Adenocarcinoma of prostate | ATCC HTB 81 Brain mets. |
| T24 | 44–46 | 75 | NT | 33.2 | 34.4 | NT | 76.3× | NT | Transitional cell ca of urinary bladder | ATCC HTB 4 |
| A549 | 80–81 | 81 | 29.0 | 28.5 | 28.1⁻ | 34.5 | 43.3 | 45.5 | Adenocarcinoma of lung | ATCC CCL 185 Primary tumor |
| Detroit 562 | 50–51 | 88 | NT | 33.2 | 36.9 | 35.9 | NT | NT | Epithelial- like carcinoma of pharynx | ATCC CCL 138 Pleural effusion |
| HOS | 49 | 71+ | 32.8 | 46.3 | 36.8 | 27.3 | NT | 65.4 | Osteosarcoma | ATCC CRL 1543 Primary tumor |
| A673 | 17 | 77+ | 76.9 | 86.1 | 88.6 | 90.1 | NT | 95.7 | Rhabdomyosarcoma | ATCC CRL 1598 15 year-old girl |
| Y79 | 27 | 74+ | 27.2 | 40.6 | 23.2 | 28.7 | NT | 72.3 | Retinoblastoma | ATCC HTB 18 Primary tumor |
| Jiyoye | 78 | 85+ | 37.0 | 50.7 | 75.3 | 18.3 | 81.3 | 81.1 | Burkitt Lymphoma | ATCC CCL 87 Ascites fluid |

P#: Passage number;
% V: Percent viability.
*NT: Not tested.
+Cells grown in RPMI 1640 with Nutridoma-HU, all others were grown in a mixture of RPMI 1640/DMEM (1:1) with 1% Nutridoma HU.
×MAb used was B108 instead of AS12;
⁻MAb used was B413 instead of KB12.

TABLE VI

EXPRESSION OF MEMBRANE-ASSOCIATED hLH, hCG AND THEIR SUBUNITS AND FRAGMENTS BY CULTURED HUMAN COLON CANCER CELLS.

| | | | MAb | | | | | | | |
|---|---|---|---|---|---|---|---|---|---|---|
| Cell line | P# | % V | A105 % α total | KB31 % hLHβ total | KB12 % hLH holo | B109 % hCG holo | AS12 % hCGβ total | AS11 % hCGβ CTP | Cell type | Source |
| SW620 | 91–94 | 76* | NT** | 34.6 | 81.9 | 13.4 | 84.2 | 91.1 | Adenocarcinoma of colon | ATCC CCL 227 Brain mets. |
| | 95 | 90* | 29.2 | 45.5 | 70.8 | 17.9 | 80.0 | 90.1 | | |
| | 98 | 87* | 34.5 | 37.1 | 80.5 | 24.8 | 85.3 | 93.4 | | |
| | 98 | 87+ | 29.0 | 37.7 | 80.6 | 24.5 | 82.4 | 92.2 | | |
| | 100 | 95+ | 63.7 | 30.3 | 74.4 | 55.7 | 70.7 | 85.3 | | |

P#: Passage number;
% V: Percent viability.
**NT: Not tested.
*Cells grown in RPMI 1640 with 1% Nutridoma-SP
+Cells grown in RPMI 1640 with 1% Nutridoma-HU

REFERENCES

1. Pierce J. G., Parsons, T. F. (1981) Glycoprotein hormones, structure and function. Ann. Rev. Biochem. 50: 465–495.
2. Hussa, R. O. (1987) The Clinical Marker hCG. Praeger Publishers, New York.
3. Hartree, A. S., Shownkeen, R. C., Stevens, V. C., Matswra, S., Ohasi, M. and Chen, H. -C. (1983) Studies of human chorionic gonadotropin-like substance of human pituitary glands and its significance. J. Endocr. 96:115–126.
4. France, J. T. (1982) The detection of ovulation for fertility and infertility. In Recent Advances in Obstetrics and Gynecoloay, Churchill Livingstone, Edinburgh and New York, pp. 215–239.
5. Krichevsky, A., Armstrong, E. G., Schlatterer, J. P., Birken, S., O'Connor, J. F., Bikel, K., Silverberg, S., Lustbader, J. W., Canfield, R. E. (1988) Preparation and characterization of antibodies to the urinary fragment of human chorionic gonadotropin β-subunit. Endocrinology 123:584–593.
6. O'Connor, J. F., Schlatterer, J. P., Birken, S., Krichevsky, A., Armstrong, E. G., McMahon, D., Canfield, R. E. (1988) Development of highly sensitive immunoassays to measure human chorionic gonadotropin, its β-subunit, and β-core fragment in urine: application to malignancies. Cancer Res 48:1361–1366.
7. Armstrong, E. G., Ehrlich, P. H., Birken, S., Schlatterer, J. P., Siris, E. S., Hembree, W. C., Canfield, R. E. (1984) Use of a highly sensitive and specific immunoradiometric assay for detection of human chorionic gonadotropin in urine of normal, nonpregnant, and pregnant individuals. J. Clin. Endocrinol. Metab. 59:867–874.
8. Soos, M., Siddle, K. (1983) Characterization of monoclonal antibodies for human luteinizing hormone. Clin. Chim. Acta. 133:263–274.
9. Alonso-Whipple, C., Couet, M. L., Doss, R., Koziarz, J., Ogunro, E. A., Crowley, W. D., Jr. (1988) Epitope mapping of human luteinizing hormone using monoclonal antibodies. Endocrinology 123:1854–1860.
10. Odell, W. D., Griffin, J. (1987) Two-monoclonal-antibody "sandwich-type" assay of human lutropin, with no cross reaction with choriogonadotropin. Clin. Chem. 33:1603–1607.
11. Ehrlich, P. H., Moyle, W. R., Moustafa, Z. A., Canfield, R. E. (1982) Mixing two monoclonal antibodies yields enhanced affinity for antigen. J. Immunol. 128:2709–2713.
12. Ehrlich, P. H., Moustafa, Z. A., Krichevsky, A., Birken, S., Armstrong, E. G., Canfield, R. E. (1985) Characterization and relative orientation of epitopes for monoclonal antibodies and antisera to human chorionic gonadotropin. Am. J. Reprod. Immunol. Microbiol. 8:48–54.
13. Coller, H. A., Coller, B. J. (1983) Statistical analysis of repetitive subcloning by the limited dilution technique with a view toward ensuring hybridoma monoclonality. Hybridoma 2:91–95.
14. Scatchard, G. (1949) The attraction of proteins to small molecules and ions. Ann. N.Y. Acad. Sci. 51:660–672.
15. Berger, P., Panmoung, W., Khaschab, D., Mayrigger, B., Wick, G. (1988) Antigenic features of human follicle stimulating hormone delineated by monoclonal antibodies and construction of an immunoradiometric assay. Endocrinology 123:2351–2359.
16. Schwarz, S., Berger, P., Wick, G. (1986) The antigenic surface of human chorionic gonadotropin as mapped by murine monoclonal antibodies. Endocrinology 118:189–197.
17. Norman, R., Poulton, T., Gard, T., Chard, T. (1985) Monoclonal antibodies to human chorionic gonadotropin: implications for antigenic mapping, immunoradiometric assays, and clinical applications. J. Clin. Endo. and Metab. 61:1031–1038.
18. Ehrlich, P. H., Moyle, W. R., Canfield, R. E. (1985) Monoclonal antibodies to gonadotropin subunits. In Methods in Enzymology Hormone Action Part I Peptide Hormones, Birnbaumer, L. and O'Malley, B. W. (eds) Academic Press, Vol. 109, pp 638–655.
19. Rebois, R. V., Fisherman, P. H. (1984) Antibodies against human chorionic gonadotropin convert the deglycosylated hormone from an antagonist to and agonist. J. Biol. Chem. 259:8087–8090.
20. Viadya, H. C., Dietzler, D. N., Ladenson, J. H. (1985) Inadequacy of traditional ELISA for screening hybridoma supernatants for murine monoclonal antibodies. Hybridoma 4:271–276.

21. Rosen, S. W., Weintraub, B. D. and Aaronson, S. A., Nonrandom ectopic protein production by malignant cells; direct evidence in vitro. J. Clin. Endocrinol. Metab. 50:834–841 (1980).
22. Bradford, M., A rapid and sensitive method for quantitation of microgram quantities of protein utilizing the principle of protein dye binding. Anal Biochem (1976); 72:248–254.

What is claimed is:

1. A method for detecting the presence of human malignant cells in a sample of tumor cells, which comprises contacting the sample with an antibody directed to an epitope present on the β subunit of human luteinizing hormone or on intact human luteinizing hormone under conditions such that the antibody forms a complex with cells present in the sample if the epitope is present on the surface of the cells, and determining whether the antibody forms such a complex, so as to thereby detect the presence of human malignant cells in the sample.

2. The method of claim 1, wherein the antibody is a monoclonal antibody.

3. The method of claim 2, wherein the monoclonal antibody is designated B406.

4. The method of claim 2, wherein the monoclonal antibody is designated B408.

5. The method of claim 2, wherein the monoclonal antibody is designated B413.

6. The method of claim 2, wherein the monoclonal antibody is designated B409.

7. A method for determining whether a tumor present in a human subject is malignant which comprises obtaining a sample of cells from the tumor and detecting the presence of malignant cells in the sample according to the method of claim 1, so as to thereby determine whether the tumor is malignant.

8. A method for obtaining an enriched population of live human malignant cells which comprises contacting a population of cells comprising live human malignant cells with an antibody directed to an epitope present on the β subunit of human luteinizing hormone or on intact human luteinizing hormone under conditions such that the antibody forms a complex with the cells present in the population if the epitope is present on the surface of the cells, and isolating the cells which form a complex with the antibody so as to obtain an enriched population of live human malignant cells.

9. The method of claim 8, wherein the antibody is a monoclonal antibody.

10. The method of claim 9, wherein the monoclonal antibody is designated B406.

11. The method of claim 9, wherein the monoclonal antibody is designated B408.

12. The method of claim 9, wherein the monoclonal antibody is designated B413.

13. The method of claim 9, wherein the monoclonal antibody is designated B409.

* * * * *